United States Patent [19]

Hsiung et al.

[11] 4,175,572
[45] Nov. 27, 1979

[54] HAIR CONDITIONING WAVING AND STRAIGHTENING COMPOSITIONS AND METHODS

[75] Inventors: Du Y. Hsiung, Park Forest; William H. Mueller, Oak Park, both of Ill.

[73] Assignee: Johnson Products Co., Inc., Chicago, Ill.

[21] Appl. No.: 818,282

[22] Filed: Jul. 22, 1977

[51] Int. Cl.² ............................................. A45D 7/00
[52] U.S. Cl. ......................................... 132/7; 424/70
[58] Field of Search ......................... 132/7; 424/70, 71

[56] References Cited

U.S. PATENT DOCUMENTS 3,912,808  10/1975  Sokol ................................... 424/71

FOREIGN PATENT DOCUMENTS 406947    3/1967  Australia ................................... 424/70
700516   12/1964  Canada ..................................... 424/70
49-69845  5/1974  Japan ...................................... 424/70

Primary Examiner—G. E. McNeill
Attorney, Agent, or Firm—Dressler, Goldsmith, Clement, Gordon & Shore, Ltd.

[57] ABSTRACT

A hair conditioner composition for use under highly alkaline conditions comprising an aqueous dispersion containing from about 1 to about 20 weight percent of mineral oil, from about 1 to about 20 weight percent of a fatty alcohol having 12 to 18 carbon atoms, from about 1 to about 15 weight percent of a non-ionic emulsifier, and from about 0.05 to 20 weight percent of a quaternary polymer having recurring units of the formula

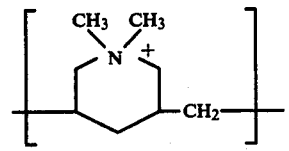

and compositions and methods for waving or straightening hair employing the above hair conditioner composition and a hair waving or straightening solution containing sufficient sodium hydroxide to provide a pH of about 12 to 13.

10 Claims, No Drawings

HAIR CONDITIONING WAVING AND STRAIGHTENING COMPOSITIONS AND METHODS

BACKGROUND OF THE INVENTION

This invention relates to hair conditioning compositions and more specifically relates to hair conditioning compositions for use with highly alkaline hair waving or straightening compositions and to methods of waving or straightening hair under highly alkaline conditions while improving the condition of the hair.

In recent years, hair straightening has become increasingly popular in view of the hair styles which require relatively or perfectly straight hair. There are several types of hair relaxers available. One type is based on the reducing agents such as sulfites or thioglycolates which react with the disulfide bond of hair keratin to form sulfhydryl or reduced hair. While the majority of home straightening kits are based on the sulfite or thioglycolate straighteners, there are several disadvantages inherent in their use. The major disadvantage is the highly offensive odor of the thioglycolate solutions, themselves, and of the reduced hair produced by either the sulfite or the thioglycolate solutions. The second disadvantage is that they require the use of an oxidizing neutralizer, such as hydrogen peroxide, to re-establish the disulfide linkages and stop the straightening process. The neutralizer must then be removed and the entire straightening process is then followed by shampooing.

Sodium hydroxide-based hair straightening or relaxer kits became available in 1958, and today, essentially all of the chemical hair straighteners used in professional shops are based on sodium hydroxide. The sodium hydroxide-based relaxer was introduced to the retail market in 1971 and has gained popularity in home use since that time. Sodium hydroxide based relaxers generally contain petrolatum and/or mineral oil to reduce their caustic effect and contain anionic surfactant and sometimes a non-ionic surfactant for improved wettability of the composition.

Fatty alcohols, lanolin, ethoxylated fatty alcohols, ethoxylated lanolin, stearic acid, and protein hydrolyzates have also been used in aqueous sodium hydroxide-based hair relaxers, in addition to color and fragrance additives.

Aside from their causticity, the principal disadvantage of sodium hydroxide-based relaxers is that they leave the hair in a brittle state and harsh to the touch.

Despite the disadvantages of the sodium hydroxide relaxers, they have several advantages over the sulfite or thioglycolate relaxing agents and would be far superior for home and beauty shop use if the problem of harshness to the hair could be overcome. The sodium hydroxide relaxers do not have a highly objectionable odor or cause such an odor by reducing the hair, and, as sodium hydroxide straightened hair is already cross-linked by a lanthionine linkage, the only step required following the straightening process is to shampoo the hair with an acidic shampoo to remove the excess alkaline solution.

Modernly, there has also been a growing demand for hair products which protect and condition the hair, leaving the hair soft and manageable as well as straightening or waving it, and a number of hair conditioning agents and compositions have been developed and marketed. Sokol, U.S. Pat. No. 3,912,808, discloses the use of certain water soluble quaternary, cationic polymers which modify the surface characteristics of hair and improve its condition, and further discloses the incorporation of the polymers in hair waving and straightening compositions based on the reducing agents capable of reducing the disulfide linkages in hair keratin, such as the odiferous thioglycolates or odor causing sulfites. However, the Sokol patent teaches that the cationic polymers may only be effectively employed in aqueous solutions of pH 1.5 to 11.5 (column 3, lines 3 to 4). We have surprisingly found that some of the polymers disclosed in the Sokol patent may be effectively employed with highly alkaline solutions of pH 12 to 13. This is unexpected as a solution of pH 12 is three times as alkaline as a solution of pH 11.5 and one would expect the cationic polymer to be adversely affected by a threefold or more increase in alkalinity.

We have also found that sodium hydroxide-based relaxing or waving solutions can be adapted for safe and effective use by incorporating therein materials which protect the users' hair.

Thus, the present invention provides a solution to a long standing need by providing improved compositions and methods employing highly alkaline straightening or waving agents.

SUMMARY OF THE INVENTION

The hair conditioner composition of this invention is adapted for use under highly alkaline conditions and comprises an aqueous dispersion containing from about 1 to about 20 weight percent of mineral oil, from about 1 to about 20 weight percent of a fatty alcohol having 12 to 18 carbon atoms, from about 1 to about 15 weight percent of a non-ionic emulsifier and from about 0.05 to about 20 weight percent of a quaternary polymer having recurring units of the formula:

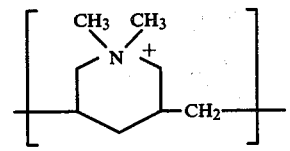

The hair conditioner is used with highly alkaline hair waving or straightening compositions based on sodium hydroxide. The conditioner can be combined with the waving or relaxing formulation prior to use, or can be applied separately to the hair either before or after application of the relaxer or waving composition.

DETAILED DESCRIPTION OF THE PREFERRED EMBODIMENTS

The hair conditioner composition of this invention comprises an aqueous dispersion containing from about 1 to about 20 weight percent, and preferably from about 3 to about 7 weight percent of mineral oil, from about 1 to about 20 weight percent and preferably from about 8 to about 12 weight percent of a fatty alcohol having 12 to 18 carbon atoms, from about 2 to about 15 weight percent and preferably from about 1 to about 10 weight percent of a non-ionic emulsifier, and from about 0.05 to about 10 weight percent, preferably from about 3 to about 5 weight percent of a quaternary polymer having recurring units of the formula:

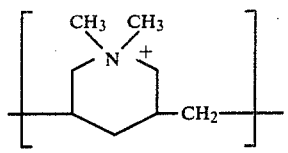

The aqueous conditioning hair relaxer or straightener composition employed in the present invention contains sufficient sodium hydroxide to provide an aqueous solution having a pH of between about 12 to about 13, generally from about 1 to about 3 weight percent, and additionally comprises from about 10 to about 30 weight percent of petrolatum, from about 1 to about 15 weight percent of mineral oil, from about 0.1 to about 5 weight percent of polyethylene, from about 1 to about 15 percent by weight of a non-ionic emulsifier, from about 1 to about 10 weight percent of propylene glycol, from about 0.5 to about 5 weight percent of polyoxyethylene lanolin ether, from about 1 to about 20 weight percent of a fatty alcohol having from 12 to 18 carbon atoms and from about 0.05 to about 10 weight percent of the quaternary polymer.

The quaternary polymer can be either a homopolymer wherein all of the groups are substantially as shown above, or a copolymer wherein at least about 50% of the recurring groups are of the structure shown above. The remaining groups are moieties of vinyl monomers, such as acrylamide. The preferred quaternary polymers have recurring units of diallyldimethylammonium salts.

The preferred polymer is a polydimethyldiallylammonium salt, such as polydimethyldiallylammonium chloride.

The homopolymers and copolymers can be prepared by polymerizing diallyldimethylammonium chloride or bromide, or other suitable diallylmonomeric ammonium salts, using a free radical generating polymerization catalyst, such as a peroxide, then employing a suitable anion exchange resin, if desired, according to the methods described in U.S. Pat. Nos. 3,288,770 and 3,412,091.

The fatty alcohols employed in the composition of this invention contain from 12 to 18 carbon atoms and include cetyl alcohol, oleyl alcohol, pentadecanol and octadecanol.

The non-ionic emulsifier employed in the hair conditioning compositions of this invention is preferably Emulsifying Wax N.F., comprising cetostearyl alchohol and containing a polyoxyethylene derivative of a fatty acid ester of sorbitan. The Emulsifying Wax is a creamy white, wax-like solid which is freely soluble in ether, chloroform, alcohol and most hydrocarbon solvents, but insoluble in water. It melts at a temperature between 48° and 52° C., has a hydroxyl value between 178 and 192, an iodine value not more than 3.5, a saponification value not more than 14, and a pH (in a dispersion of 3 parts in 100 parts of water) between 5.5 and 7.0.

Other suitable non-ionic emulsifiers include polyethylene glycol esters of fatty acids, polyoxyethylene ethers of fatty alcohols, polyethylene oxide-polypropylene oxide condensates, and polyoxyethylene lanolin ether.

The term "highly alkaline", as used herein, refers to pH 12.0 to 13.0.

In the practice of this invention, the hair conditioning composition disclosed herein can be applied to the hair prior to the application of the relaxer, can be premixed with the relaxer and applied at the same time, or can be applied after application of the relaxer to the hair. The conditioner is preferably left on the user's head for at least 12 minutes, preferably from 12 to 20 minutes, and the relaxer for from 12 to 20 minutes.

After the conditioning and straightening or waving process has been completed, an acidic shampoo is employed to remove the excess alkaline solution.

The following examples further illustrate the present invention.

EXAMPLE I

A hair conditioning composition was prepared having the following composition:

| Ingredient | Weight Percent |
| --- | --- |
| Cetyl alcohol | 10.0 |
| Emulsifying Wax | 7.0 |
| Mineral oil | 5.0 |
| Polydiallyldimethylammonium chloride | 4.0 |
| Water to | 100.0 |

EXAMPLE II

A hair relaxer or straightening preparation was formulated having the following composition:

| Ingredient | Weight Percent |
| --- | --- |
| Sodium hydroxide | 2.2 |
| Petrolatum | 26.0 |
| Mineral oil | 9.5 |
| Polyethylene (1500 M.W.) | 1.0 |
| Emulsifying Wax | 10.0 |
| Propylene glycol | 5.5 |
| Polyxyethylene lanolin ether | 1.0 |
| Water to | 100.0 |

EXAMPLE III

A conditioning hair relaxer was prepared having the following composition:

| Ingredient | Weight Percent |
| --- | --- |
| Petrolatum | 26.0 |
| Mineral oil | 9.5 |
| Polyethylene (1500 M.W.) | 1.0 |
| Emulsifying Wax | 10.0 |
| Propylene glycol | 5.5 |
| Sodium hydroxide | 2.2 |
| Polyoxyethylene lanolin ether | 1.0 |
| Polydiallyldimethylammonium chloride | 0.25 |
| Water to | 100.0 |

EXAMPLE IV

A conditioning hair relaxer was prepared having the following composition:

| Ingredient | Weight Percent |
| --- | --- |
| Petrolatum | 26.0 |
| Mineral oil | 9.5 |
| Polyethylene (1500 M.W.) | 1.0 |
| Emulsifying Wax | 10.0 |
| Propylene glycol | 5.5 |
| Sodium hydroxide | 2.2 |
| Polyoxyethylene lanolin ether | 1.0 |
| Diallyldimethylammonium chloride-acrylamide copolymer | 0.5 |

| Ingredient | Weight Percent |
|---|---|
| Water to | 100.0 |

EXAMPLE V

Seven ounces of the hair relaxer of Example II was mixed with ½ ounce of the hair conditioner of Example I and applied to one-half of 38 heads of hair. After 12 to 18 minutes from the time of initial application, the hair was shampooed three times with an acidic shampoo. The hair relaxer only was applied to the other side of the test heads.

After shampooing, the sides straightened with the conditioning relaxer exhibited less tangling, were easier to comb when both wet and dry and were softer, silkier and smoother than the control sides (relaxer only). Good straightening was observed on both sides.

EXAMPLE VI

One-half ounce of the hair conditioner of Example I was applied to one-half of four models' heads and distributed throughout the hair on the test side. Three and one-half ounces of the hair relaxer of Example II was then added to each side of the heads and smoothed through the hair. After 12 to 18 minutes after the initial application of the relaxer, the hair was shampooed three times with an acidic shampoo. The hair on the sides treated with conditioner and relaxer exhibited less tangling, was easier to comb and was softer, silkier and smoother than the control sides treated with relaxer alone.

EXAMPLE VII

The conditioning hair relaxing composition of Example III was applied to the hair, smoothed through and washed off 18 minutes after the initial application time with an acidic shampoo. The same conditioning advantages observed in Examples V and VI were observed.

What is claimed is:

1. A hair conditioning composition for use under highly alkaline conditions comprising an aqueous dispersion containing from about 1 to about 20 weight percent of mineral oil, from about 1 to about 20 weight percent of a fatty alcohol having 12 to 18 carbon atoms, from about 1 to about 15 weight percent of a non-ionic emulsifier, and from about 0.05 to about 20 weight percent of a quaternary polymer having recurring units of the formula:

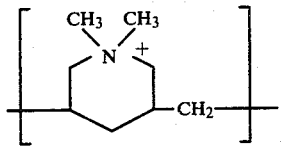

2. The composition of claim 1 wherein said nonionic emulsifyer is selected from the class consisting of Emulsifying Wax N.F., polyethylene glycol esters of fatty acids, polyoxyethylene ethers of fatty alcohols, polyethylene oxide-polypropylene oxide condensates, and polyoxyethylene lanolin ether.

3. The hair conditioner composition of claim 2 wherein said quaternary polymer is a homopolymer wherein all of the groups are substantially as shown.

4. The hair conditioner composition of claim 2 wherein said quaternary polymer is a copolymer wherein at least about 50% of the groups are substantially as shown, and the remainder are acrylamide moieties.

5. The hair conditioner composition of claim 2 wherein said quaternary polymer is polydiallyldimethylammonium chloride.

6. The hair conditioner composition of claim 2 wherein said mineral oil is present in an amount from abut 3 to 7 weight percent, said fatty alcohol is cetyl alcohol and is present in an amount from about 8 to 12 weight percent and said non-ionic emulsifier is Emulsifying Wax N.F. and is present in an amount from about 5 to about 10 weight percent.

7. A method of straightening or waving hair which comprises applying to said hair the composition of claim 1, thereafter applying to said hair an aqueous dispersion containing petrolatum and a sufficient concentration of sodium hydroxide to provide in said aqueous dispersion a pH between about 12 and about 13, placing said hair in a desired configuration and thereafter shampooing said hair with an acidic shampoo composition to neutralize excessive alkalinity.

8. The method of claim 7 wherein said quaternary polymer of the composition of claim 1 is polydiallyldimethylammonium chloride.

9. A hair conditioner composition for use under highly alkaline conditions comprising an aqueous dispersion containing about 5 weight percent of mineral oil, about 10 weight percent of cetyl alcohol, about 7 weight percent of Emulsifying Wax N.F., and about 4 weight percent of polydiallyldimethylammonium chloride.

10. A composition for waving or straightening hair comprising an aqueous dispersion containing from about 1 to about 20 weight percent of mineral oil, from about 1 to about 20 weight percent of a fatty alcohol having 12 to 18 carbon atoms, from about 1 to about 15 weight percent of a non-ionic emulsifier, from about 0.05 to about 20 weight percent of a quaternary polymer having recurring units of the formula:

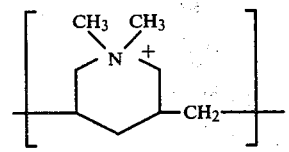

from about 10 to about 30 weight percent of petrolatum, from about 1 to about 10 weight percent of a normal liquid polyhydroxy compound, and from about 1 to about 3 weight percent of a watersoluble alkaline caustic material, the composition having a pH between about 12 and about 13.

* * * * *